United States Patent [19]

Ohsumi et al.

[11] 4,212,829
[45] Jul. 15, 1980

[54] PREPARATION OF M-(P-BROMOPHENOXY)BENZALDEHYDE

[75] Inventors: Tadashi Ohsumi, Kyoto; Nobushige Itaya, Nishinomiya, both of Japan

[73] Assignee: Sumitomo Chemical Compamy, Limited, Osaka, Japan

[21] Appl. No.: 5,170

[22] Filed: Jan. 22, 1979

[30] Foreign Application Priority Data

Jan. 25, 1978 [JP] Japan .................................. 53/7760

[51] Int. Cl.$^2$ .............................................. C07C 45/00
[52] U.S. Cl. ..................................... 568/433; 568/442
[58] Field of Search ..................................... 260/600 R

[56] References Cited

U.S. PATENT DOCUMENTS

| 3,689,559 | 9/1972 | Taylor eet al. | 260/600 X |
| 3,855,306 | 12/1974 | Wehrli | 260/600 R |
| 3,996,291 | 12/1976 | Dietrich et al. | 260/600 R |
| 4,085,147 | 4/1978 | Rosinger et al. | 260/600 R |

FOREIGN PATENT DOCUMENTS 853411 9/1976 Belgium .

OTHER PUBLICATIONS

Derwent, Central Patents Index, 72509Y/41.

Primary Examiner—Bernard Helfin
Attorney, Agent, or Firm—Stevens, Davis, Miller & Mosher

[57] ABSTRACT

A process for preparing m-(p-bromophenoxy)benzaldehyde of the formula,

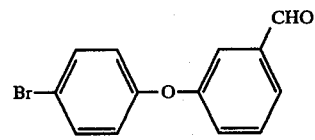

characterized by brominating m-phenoxybenzaldehyde with bromine or bromine chloride as a brominating agent.

3 Claims, No Drawings

PREPARATION OF M-(P-BROMOPHENOXY)BENZALDEHYDE

The present invention relates to a process for the production of m-(p-bromophenoxy)benzaldehyde of the formula,

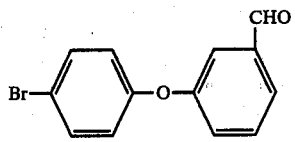

and more particularly it relates to the selective bromination of m-phenoxybenzaldehyde.

In general, the halogenation of aromatic hydrocarbons with a halogen is a well-known reaction, but this reaction requires a catalyst in many cases and produces isomers as by-product which often make the operation troublesome because of the need for their separation. Particularly, an industrial, direct halogenation which is carried out without protecting highly reactive functional groups such as an aldehyde group, as intended in the present invention, has never been established. In many cases, the halogenation is carried out after protecting the aldehyde group with aluminum chloride or the like.

As is described in D. E. Pearsons: J. Org. Chem. 23, 1412 (1958), for example, it is common that the halogenation of aromatic aldehydes produces an acid halide when a catalyst is not used, while it produces a nuclear-halogen derivative only when a catalyst such as silver sulfate is used. Particularly, from the description in the above literature that the use of an equivalent weight or more of aluminum chloride based on benzaldehyde is essential to nuclear halogenation, it is easily understandable that the process of the present invention is not a common reaction and can never be easily analogized.

Further, in order to demonstrate that the process of the present invention is one which makes the most use of the structural characteristics of the compound itself, chlorination of the compound was carried out as follows in a similar manner to the process of the present invention: Chlorine gas was passed through a solution of m-phenoxybenzaldehyde in a solvent. The results are shown in Table 1.

As can be seen from the table, this reaction produces an isomer, m-(o-chlorophenoxy)benzaldehyde, as by-product together with large amounts of impurities. This tendency is improved to some extent by lowering the reaction temperature, but the problems such as low yield of the objective compound and formation of m-(o-chlorophenoxy)benzaldehyde as by-product still remain unsolved. Particularly, the formation of the by-product, m-(o-chlorophenoxy)benzaldehyde, makes it difficult to remove the by-product from the objective compound, m-(p-chlorophenoxy)benzaldehyde. For example, purification by distillation is very difficult because of the similar boiling point of both compounds, and chemical purification with sodium hydrogen sulfite can not be an effective means because of almost the same behaviour of the both compounds to that chemical. In order to improve the position selectivity and yield, the catalytic effect of ferric chloride, zinc chloride and titanium chloride was investigated. Good results were not however obtained: The pure yield was slightly improved but the amount of m-(o-chlorophenoxy)benzaldehyde increased, as is apparent from Table 1. Further, solvent effect was also investigated to some degree, but chlorobenzene and tetrachloroethylene were inferior to methylene chloride in the position selectivity and pure yield.

From the fact previously found by the inventors that the conventional pyrethroid type insecticides having a halogen atom at the p-position show a great reduction in toxicity to fishes, the inventors extensively studied to obtain m-phenoxybenzaldehyde having a halogen atom at the p-position which is a useful intermediate for the production of these pyrethroid type insecticides (Kasamatsu et al.: Japanese Patent Application Nos. 125420/1978, 125421/1978, 85714/1978, 71489/1977 and 69119/1977). As a result, it was found unexpectedly that the bromination of m-phenoxybenzaldehyde proceeds with an extremely high selectivity and a high yield. The inventors thus attained to the present invention.

m-Phenoxybenzaldehyde used as a starting material in the present invention can easily be produced, for example, by the processes disclosed in Japanese Patent Application Kokai (Laid-Open) Nos. 143638/1976, 40732/1978, 82736/1978 and 112824/1978. This compound is already commercially available as an intermediate for many pyrethroid type insecticides of economical importance and extreme effectiveness. It is therefore apparent that the process of the present invention makes it possible to produce the objective compound at low cost and with extreme ease of operation, high yield and high selectivity as clearly shown in the examples, and therefore is far superior to other processes in economy and operation.

In the present invention, the bromination of m-phenoxybenzaldehyde may be carried out in the presence or absence of a solvent. However, it is preferably carried out in a halogenation-resistant solvent at a temperature lower than the boiling point of the solvent, preferably lower than room temperature. The solvent includes methylene chloride, tetrachloroethylene, chlorobenzene and the like. Catalysts are not required at all in general, but the reaction is not hindered even though a metal halide such as aluminum chloride, ferric chloride, zinc chloride or the like is present in the system.

The completion of the reaction can easily be determined by the gas-chromatographical examination of the disappearance of the material. The objective m-(p-bromophenoxy)benzaldehyde can be obtained in a high purity and with high yield by merely removing the solvent by evaporation.

The results of the experimental bromination of m-phenoxybenzaldehyde according to the present invention are shown in Table 2. As is apparent from the table, the bromination proceeds smoothly without special heating even in the absence of a catalyst, and besides it shows an extremely high selectivity without being accompanied by m-(o-bromophenoxy)benzaldehyde as by-product.

Neither an increase in the o-isomer nor a remarkable effect on the pure yield are observed, unlike the chlorination, even though a metallic salt such as ferric chloride, aluminum chloride, zinc chloride or the like is present as a catalyst in the system. Further, in the present invention, tetrachloroethylene and chlorobenzene may be used as a solvent with the same good result as with methylene chloride.

The bromination of the present invention may be carried out using not only a bromine molecule but also bromine chloride as a brominating agent. The result is shown in Table 2.

Bromine chloride has the defect that the pure yield is low as compared with the bromine molecule, but it is advantageous in cost and retention of the high selectivity. The crude product obtained by these methods can be purified into m-(p-bromophenoxy)benzaldehyde of higher purity by distillation or the like.

Next, the present invention will be illustrated in more detail with reference to the following reference examples and examples. Examples and reference examples other than those mentioned below were carried out and their results are shown in Tables 1 and 2.

REFERENCE EXAMPLE 1

9.90 Grams (0.050 mole) of m-phenoxybenzaldehyde were dissolved in 40 ml of methylene chloride, and chlorine gas was passed through the resulting solution at 0° C. for 30 minutes. After the reaction was finished, the reaction solution was treated in the same manner as in Example 1 (No. ii in Table 1).

Yield: 11.54 g (99.2% of the theoretical amount)

EXAMPLE 1

9.90 Grams (0.050 mole) of m-phenoxybenzaldehyde were dissolved in 40 ml of methylene chloride, and a solution of 9.60 g (0.060 mole) of bromine in 10 ml of methylene chloride was added dropwise to the resulting solution at 0° C. taking a period of 1 hour with stirring. After the addition was finished, the reaction was continued for a further 3 hours at the same temperature. The reaction solution was washed with water and then with a dilute aqueous potassium sulfite solution to decompose bromine in the organic layer. The organic layer obtained was washed with a dilute aqueous sodium carbonate solution and then a dilute aqueous sodium chloride solution followed by drying over anhydrous sodium sulfate and concentration. (No. 2 in Table 2).

Yield: 12.95 g (93.5% of the theoretical amount)

b.p.: 130°–135° C. (0.12 mmHg)

EXAMPLE 2

0.41 Gram (0.0025 mole) of anhydrous ferric chloride was added to a solution of 9.90 g (0.050 mole) of m-phenoxybenzaldehyde in 40 ml of methylene chloride to obtain a homogeneous solution. Thereafter, a solution of 9.60 g (0.060 mole) of bromine in 10 ml of methylene chloride was added dropwise to the solution at 0° C. taking a period of 1 hour with stirring. The reaction solution was then treated in the same manner as in Example 1 (No. 3 in Table 2).

Yield: 12.62 g (91.1% of the theoretical amount)

EXAMPLE 3

9.90 Grams (0.050 mole) of m-phenoxybenzaldehyde was dissolved in 40 ml of methylene chloride. Separately from this, 4.80 g (0.030 mole) of bromine and 1.78 g (0.025 mole of chlorine were reacted at −20° C. in methylene chloride to prepare a solution of bromine chloride in mehtylene chloride. This solution was added dropwise to the above solution at −30° C. taking a period of 30 minutes with stirring. After the addition was finished, the reaction was continued for a further 30 minutes at the same temperature. The reaction solution was treated in the same manner as in Example 1 (No. 8 in Table 2).

Yield: 13.29 g (96.0% of the theoretical amount)

EXAMPLE 4

9.60 Grams (0.060 mole) of bromine were added dropwise to 9.90 g (0.050 mole) of m-phenoxybenzaldehyde at 0° C. taking a period of 1 hour with vigorous stirring. After the addition was finished, the reaction was continued for a further 3 hours at the same temperature. The unreacted bromine was distilled off under reduced pressure from the reaction system to obtain m-(p-bromophenoxy)benzaldehyde (No. 9 in Table 2).

Yield: 13.14 g (94.9% of the theoretical amount)

Table 1

| No. | Temperature | Catalyst (mole %, based on m-phenoxybenzaldehyde) | | Unreacted m-phenoxybenzaldehyde (%) | m-(o-Chlorophenoxy-benzaldehyde (%) | m-(p-Chlorophenoxy-benzaldehyde (%) | Pure yield (%) |
|---|---|---|---|---|---|---|---|
| i | −15° C. | — | Methylene chloride | <0.1 | 4.5 | 71.7 | 68.3 |
| ii | 0° C. | — | Methylene chloride | <0.1 | 4.5 | 65.4 | 64.9 |
| iii | 20° C. | — | Methylene chloride | <0.1 | 3.5 | 57.4 | 59.1 |
| iv | −15° C. | FeCl$_3$(5 mole %) | Methylene chloride | <0.1 | 8.5 | 75.7 | 73.8 |
| v | −15° C. | FeCl$_3$(2.5 mole %) | Methylene chloride | <0.1 | 7.7 | 76.2 | 72.2 |
| vi | 0° C. | FeCl$_3$(5 mole %) | Methylene chloride | <0.1 | 11.2 | 73.2 | 70.2 |
| vii | 0° C. | ZnCl$_2$(5 mole %) | Methylene chloride | <0.1 | 8.9 | 73.0 | 70.1 |
| viii | 0° C. | AlCl$_3$(5 mole %) | Methylene chloride | <0.1 | 8.1 | 67.3 | 62.3 |
| ix | −15° C. | TiCl$_4$(5 mole %) | Methylene chloride | <0.1 | 5.8 | 70.6 | 68.3 |
| x | −15° C. | AlCl$_3$(equivalent weight) | Methylene chloride | <0.1 | 17.6 | 58.2 | 55.5 |
| xi | 0° C. | — | Chlorobenzene | <0.1 | 3.8 | 48.0 | 54.2 |
| xii | −15° C. | — | Tetrachloroethylene | <0.1 | 9.8 | 61.6 | 62.5 |

Table 2

| No. | Temperature | Catalyst (mole %, based on m-phenoxybenzaldehyde) | Solvent | Unreacted m-phenoxy)-benzaldehyde (%) | m-(o-Bromo-phenoxy)-benzaldehyde (%) | m-(p-Bromo-phenoxy)-benzaldehyde (%) | pure yield (%) |
| --- | --- | --- | --- | --- | --- | --- | --- |
| 1 | 20° C. | — | Methylene chloride | 0.1 | <0.1 | 91.4 | 85.1 |
| 2 | 0° C. | — | Methylene chloride | 0.1 | <0.1 | 92.8 | 86.8 |
| 3 | 0° C. | FeCl$_3$(5 mole %) | Methylene chloride | 0.1 | <0.1 | 92.3 | 84.1 |
| 4 | 0° C. | AlCl$_3$(5 mole %) | Methylene chloride | 0.1 | <0.1 | 93.0 | 87.0 |
| 5 | 0° C. | ZnCl$_2$(5 mole %) | Methylene chloride | 0.1 | <0.1 | 92.8 | 85.5 |
| 6 | 0° C. | — | Tetrachloroethylene | 0.1 | <0.1 | 92.5 | 86.3 |
| 7 | 0° C. | — | Chlorobenzene | 0.1 | <0.1 | 92.3 | 86.5 |
| 8 | −30° C. | BrCl (as brominating agent) | Methylene chloride | 0.1 | <0.1 | 84.9 | 81.5 |
| 9 | 0° C. | — | — | 0.1 | <0.1 | 88.1 | 83.6 |

What is claimed is:

1. A process for preparing m-(p-bromophenoxy)benzaldehyde of the formula;

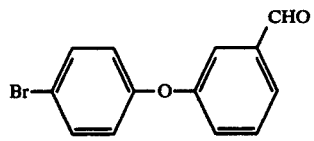

which comprises slowly adding bromine or bromine chloride to m-phenoxybenzaldehyde at room temperature or below.

2. The process according to claim 1, wherein the bromination is carried out in a halogenation-resistant solvent.

3. The process according to claim 1, wherein the reaction is carried out in the presence of ferric chloride, aluminum chloride or zinc chloride as a catalyst.

* * * * *